United States Patent
Waller et al.

(10) Patent No.: US 6,201,038 B1
(45) Date of Patent: Mar. 13, 2001

(54) HYDROPHILICALLY MODIFIED CURABLE SILICONE IMPRESSION MATERIAL

(75) Inventors: Duncan E. Waller, Ypsilanti, MI (US); Xiaoyi Xie, San Gabriel, CA (US)

(73) Assignee: Kerr Corporation, Orange, CA (US)

( * ) Notice: Subject to any disclaimer, the term of this patent is extended or adjusted under 35 U.S.C. 154(b) by 0 days.

(21) Appl. No.: 09/250,927

(22) Filed: Feb. 18, 1999

(51) Int. Cl.⁷ .............................. A61K 6/10; C08L 83/12; C08L 83/04

(52) U.S. Cl. ................ 523/109; 524/375; 524/376; 524/378; 524/588; 524/847; 524/862; 528/15; 528/18

(58) Field of Search ............................ 523/109; 524/375, 524/376, 378, 588, 847, 862; 528/15, 18

(56) References Cited

U.S. PATENT DOCUMENTS 6,013,711 * 1/2000 Lewis et al. ..................... 524/265

* cited by examiner

*Primary Examiner*—Robert Dawson
*Assistant Examiner*—Jeffrey B. Robertson
(74) *Attorney, Agent, or Firm*—Wood, Herron & Evans, LLP

(57) ABSTRACT

The present invention provides hydrophilically modified curable silicone dental impression materials comprising an addition curable silicone prepolymer composition and a polymerizable hydrophilic modifier. The addition curable silicone prepolymer in the composition of the present invention comprises blended vinyl terminated organopolysiloxane fluids, an organohydrogen polysiloxane crosslinker, a platinum catalyst, a retarder, filler and optional additives. The cured compositions have a stable hydrophilic nature, excellent mechanical properties, and maximum long-term dimensional stability.

33 Claims, No Drawings

HYDROPHILICALLY MODIFIED CURABLE SILICONE IMPRESSION MATERIAL

FIELD OF THE INVENTION

This invention relates to a curable silicone impression material, in particular, a dental impression material having a stable hydrophilic nature, excellent mechanical properties, and maximum long-term dimensional stability.

BACKGROUND OF THE INVENTION

Curable silicone compositions, especially the addition-curable silicone compositions, are widely used as dental impression materials. Generally, the addition-curable silicone compositions have the advantages of fast curing speed and low shrinkage. Furthermore, the cured silicone compositions have excellent physical properties, such as high mechanical strength and good dimensional stability. A considerable disadvantage of silicone compositions of this type, however, is their high hydrophobicity, which makes it difficult for them to take precise impressions when used on wet surfaces, such as the tissue, tooth or dental prosthesis in the oral environment in which blood, saliva, or other fluids usually exist.

The preparation of dental silicone impression materials by incorporating hydrocarbon, fluorocarbon or silicone-based surfactants, including ionic- and nonionic-type surfactants is known for imparting hydrophilic properties to these inherently hydrophobic substances and for improving the surface wettability. However, the addition of one or more surfactants to the compositions of the silicone polymers to impart hydrophilicity has drawbacks in that the surfactant molecules have a tendency to demix from the impression materials or migrate to the surface thereof, or the molecules are extracted from the impression material when it is contacted with aqueous media. Thus, the hydrophilicity of the impression materials cannot be retained when subjected to the procedures of rinsing with water, disinfection and sterilization required in dental clinic practice. Furthermore, when the surfactant is added in a large amount to obtain satisfactory water wettability of the cured silicone composition, the curing reaction of the composition is hindered, and the cured silicone composition has poor physical properties such as low tensile strength, elongation and tear strength. Particularly, the loss of surfactant due to contact with aqueous media results in undesirable dimensional change of the cured silicon composition.

Attempts have been made to render silicone dental impression materials more hydrophilic by adding hydrophilic additives into the curable silicone compositions. Hittmair et al. in U.S. Pat. No. 4,035,453 discloses the methods of making dental impression materials using curable silicone compositions. Bryan et al. in U.S. Pat. No. 4,657,959 and Aasen et al. in U.S. Pat. Nos. 4,691,039 and 4,752,633 disclose adding an ethoxylated nonionic surfactant containing siloxane or perfluoroalkyl solubilizing groups to achieve a three-minute water contact angle below about 65°. Fujiki et al. in U.S. Pat. No. 5,064,891 discloses a curable silicone composition comprising a nonionic surface active agent having a hydrophobic silicone portion and at least one hydrophilic polyol portion in its molecule. Kamohara et al. in U.S. Pat. No. 5,637,628 discloses a dental impression-taking silicone composition comprising a polyvinyl ether having a degree of polymerization of 1,000 to 50,000. Hare in U.S. Pat. Nos. 5,661,222 and 5,863,965 and Fiedler in U.S. Pat. No. 5,830,951 disclose two-component polymerizable polyvinylsiloxane compositions comprising mono- and quadri-functional resins (QM) and nonylphenoxypoly (ethyleneoxy) ethanol surfactant. Zech et al. in U.S. Pat. No. 5,750,589 discloses a dental impression material containing polyether carbosilane as a hydrophilation agent. Jada in U.S. Pat. No. 5,852,068 discloses a dental impression composition comprising a dimethicone-based polysiloxane polyester polymer having terminal fluorinated alkoxy substituents. Paradiso in WO 93/17654 discloses a dental impression material comprising mono and quadri-functional QM resins. Gribi in EP 0 231 420 B1 describes the use of siloxane components having polyether moieties in the molecule.

The prior art hydrophilic additives in the silicone impression compositions suffer from certain drawbacks including unstable hydrophilicity when in contact with aqueous media and reduction in the physical properties such as tensile strength, elongation and tear strength. Accordingly, it would be desirable to provide an improved curable silicone impression material having a stable hydrophilic nature, excellent mechanical properties, and maximum long-term dimensional stability.

SUMMARY OF THE INVENTION

The present invention provides a curable silicone composition comprising a mixture of: (a) an addition-curable silicone prepolymer; and (b) at least one polymerizable hydrophilic modifier that is a functional hydrophilic polysiloxane having the general formula:

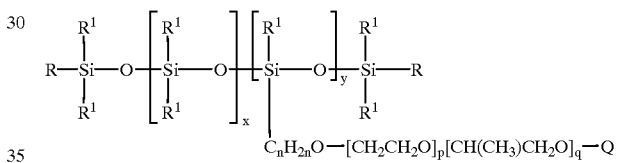

wherein functional group R is a vinyl group or a hydrogen atom; $R^1$ is a $C_1$ to $C_8$ univalent hydrocarbon radical; Q is a hydrogen atom or a monovalent hydrocarbyl radical; n is an integer greater than or equal to three; x is an integer greater than or equal to zero; y is an integer greater than or equal to one; p is an integer greater than or equal to one; and q is an integer greater than or equal to zero.

The present invention further provides a method for making a dental impression comprising the step of making a negative mold of oral tissue using a hydrophilically modified curable silicone composition of the present invention.

These and other objects and advantages of the present invention shall become more apparent from the following description.

DETAILED DESCRIPTION

The hydrophilically modified silicone impression material of the present invention is characterized by good wettability, excellent physical strength, and maximum long-term dimensional stability.

In the composition of the present invention, the hydrophilically modified silicone impression material is a two component room temperature vulcanization (RTV) addition cure vinyl polysiloxane material. The composition of the present invention in general comprises a mixture of an addition-curable silicone prepolymer and a polymerizable hydrophilic modifier. The addition-curable silicone prepolymer typically comprises the following components: (a) at least one vinyl terminated organopolysiloxane fluid having at least about two vinyl groups per molecule; (b) at least one organohydrogen polysiloxane crosslinker having at least about three silicon hydride groups per molecule; (c) a platinum catalyst; (d) a retarder; (e) filler; and (f) optional additives.

The composition of the present invention preferably comprises a catalyst paste and a base paste in intimate admixture with one another in a paste/paste system in which curing is initiated by means of a platinum-catalyzed hydrosilation (addition) reaction between the vinyl-functional polysiloxane and the hydride-functional polysiloxane crosslinker. Generally, the catalyst paste comprises vinyl terminated organopolysiloxane fluid, a platinum catalyst for accelerating the addition reaction, a retarder for delaying the curing to ensure a sufficient working time, a hydrogen scavenger for entrapping hydrogen released during polymerization, fillers for reinforcing and/or non-reinforcing (extending) purposes, and pigments. The base paste generally comprises vinyl terminated organopolysiloxane fluid, an organohydrogen polysiloxane crosslinker, a hydrophilic modifier, fillers, and pigments.

The vinyl terminated organopolysiloxanes having at least about two vinyl groups per molecule are well-known to those of ordinary skill in the art. Preferred for use herein are linear vinyl terminated organopolysiloxanes. Most commonly-used vinyl terminated organopolysiloxanes have a methyl substituent, for example, vinyl terminated polydimethylsiloxane. Other substituents such as alkyl, aryl, halogen, and the like may also be included for any particular application of the composition in accordance with the principles of this invention. The commercial vinyl terminated polydimethylsiloxanes have a wide variety of molecular weights with viscosities ranging from about 100 to about 1,000,000 centistoke. However, when the viscosity is too high, the vinyl terminated polydimethylsiloxane fluid is too viscous to formulate into free flowing dental impression materials, which is necessary for easy mixing and handling. In practice, it has been found that suitable vinylpolysiloxane fluids with viscosity lower than about 100,000 centistoke may be successfully blended with suitable fillers and other desirable additives to produce superior dental impression materials. Preferably, a blend of vinylpolysiloxane fluids having different viscosities ranging from about 100 to about 60,000 centistoke is used to provide compositions having a desired thixotropicity and viscosity, and more importantly to provide cured compositions having desired physical properties. The lower viscosities within this range contribute to higher crosslink densities and provide elastomer stiffness and high deformation recovery, while the higher viscosities within the range provide for higher elasticity and elongation.

The organohydrogen polysiloxane crosslinker useful in the composition of the present invention is organopolysiloxane having at least three hydrogen atoms per molecule directly bonded to silicon atoms. The most commonly-used organohydrogen polysiloxane crosslinkers have a methyl substituent, for example, polymethylhydrosiloxane, methylhydro dimethyl polysiloxane copolymers, and combinations thereof. Other substituents such as alkyl, aryl, halogen, and the like may also be employed for any particular application of the composition in accordance with the principles of this invention. Preferably, the polymethylhydrosiloxane has a viscosity range of about 2 to about 300 centistoke, and most preferably about 3 to about 45 centistoke.

One type of catalyst useful for catalyzing the addition reaction between the vinyl-functional polysiloxane molecules and the hydride-functional polysiloxane crosslinkers is a platinum-based catalyst. In this regard, it is preferred to employ a platinum compound such as chloroplatinic acid. The concentration of platinum and platinum compounds ranges from about 5 ppm to about 500 ppm, preferably about 5 ppm to about 200 ppm, based on the weight of the catalyst component. Preferably, the platinum and platinum compounds are used in admixture or complex with one or more vinyl-containing molecules, especially vinyl polysiloxanes in a concentration range of about 0.1 wt. % to about 5 wt. % platinum, preferably about 0.5 wt. % to about 2 wt. %. Other catalysts useful in the practice of the present invention are those based on other noble metals including palladium, rhodium, and the like, and their respective complexes and salts. In view of the toxicological acceptability of platinum, however, it is preferred for dental use.

A retarder is provided in the composition of the present invention for delaying the onset of the addition reaction between the vinyl-functional polysiloxane and the hydride-functional polysiloxane crosslinker such that sufficient working time for mixing and applying the composition is achieved. The retarder functions, as it is consumed, as a "chain stopper" to provide sufficient induction time and to allow seating of the impression tray over the dentition prior to the occurrence of any significant increase in viscosity of the mixed paste. The preferred work time is greater than 1 minute and less than 5 minutes, and preferably about 1 to 2 minutes. Suitable retarders are any low molecular weight, vinyl functional linear or cyclic polysiloxane fluid that would be initially consumed in the polymerization reaction to delay curing for the desired time period. The preferred retarder fluid is 1,3,5,7-tetravinyltetramethylcyclotetrasiloxane, which is present in the composition at a sufficient concentration level to perform its retarding functions. The preferred retarder is present at a concentration of at least about 0.01 wt. % of the composition, and preferably at a concentration within a range of about 0.01 to about 0.10 wt. %. Another suitable retarder fluid is 1,3-divinyltetramethyldisiloxane.

The fillers useful in the composition of the present invention include reinforcing and/or non-reinforcing (extending) fillers. Suitable reinforcing fillers include fumed silica, carbon black, and the like. The addition of reinforcing filler improves the mechanical strength, such as the tensile and tear strengths, of the cured silicone composition. Suitable non-reinforcing fillers include precipitated silicas, diatomaceous earth, aluminas, magnesias, titanium dioxide, zirconium silicate, calcium carbonate, metallic oxides, and the like. Surface-treated fillers may also be used. Typical surface treatments includes silanization and the like. In accordance with the principles of the present invention, it is preferable to employ mixtures of fillers with different particle sizes. Preferably, a bimodal filler system blended with sub-micron (<1 $\mu$m) and micron sized particles (2–10 $\mu$m) of close particle size distribution is used as a varying filler loading to provide dental impression materials with low, medium or high consistency suitable for use in all known dental impression techniques. The fillers are present, preferably, in amounts of from about 15 wt. % to about 50 wt. % of the composition. To adjust the consistency of the two-component composition to achieve either a low, medium or high consistency composition, the sub-micron sized filler and/or the micron sized filler may be adjusted in one or both of the catalyst and base pastes. The higher the consistency desired, the more beneficial it is to increase the sub-micron filler to a greater extent than the increase in the micron sized filler, whereby the sub-micron filler particles are worked into the interstitial spaces between micronized particles during mixing.

An optional hydrogen scavenger in the composition of the present invention is useful in controlling or preventing the presence of hydrogen gas that is evolved from the reaction from existing in the cured composition. The preferred hydrogen scavenger is a finely-divided platinum metal as described in U.S. Pat. No. 4,806,575, which is incorporated herein by reference in its entirety. Generally, the platinum metal is used at a concentration level of about 0.2 ppm to about 20,000 ppm, based on the weight of the catalyst component. The finely divided platinum metal may be added alone or may be blended with fillers described above, for example, calcium silicate, in a concentration range of about 0.1 wt. % to about 5 wt. %, and preferably about 0.5 wt. % to about 2 wt. %. Another suitable hydrogen scavenger is palladium metal as described in U.S. Pat. No. 5,684,060, which is incorporated herein by reference in its entirety.

A key improvement of the present invention is the use of a polymerizable hydrophilic modifier that imparts wettability to the composition of the present invention. The hydrophilic modifier contains hydrophobic groups and hydrophilic groups in the molecule structure. The hydrophobic groups are one or more siloxane groups that render the modifier composition soluble or dispersible in the silicone prepolymer. The hydrophilic groups are water-loving groups that render the composition of the present invention hydrophilic. The water-loving groups are ethyleneoxy ($-C_2H_4O-$) groups or propyleneoxy ($-C_3H_6O-$) groups. In the preferred composition of the present invention, the hydrophilic modifier contains polymerizable functional groups having one or more vinyl groups or one or more hydrogen atoms which directly bond to the silicon atoms of the polysiloxane molecules. One advantage of the polymerizable hydrophilic modifier is its ability to be incorporated into the cured polysiloxane matrix formed by the addition curing reaction between the vinyl terminated organopolysiloxane and the organohydrogen polysiloxane crosslinker. Therefore, curing the composition of the invention immobilizes the hydrophilic component and forms a silicone polymer material including a hydrophilic constituent, preferably in an amount effective to provide enhanced or increased hydrophilicity to the cured material, for example, relative to a substantially identical material without the hydrophilic constituent. The hydrophilic constituent in the cured material does not demix from the impression composition nor migrate to the surface thereof, and it is not extracted from the impression material when it is contacted with aqueous media. The hydrophilicity of the cured material remains substantially unchanged after relatively long contact with an aqueous system, for example, rinsing with water, disinfection and sterilization. More importantly, the cured material retains excellent physical properties such as tensile strength, elongation, tear strength and dimensional stability.

The polymerizable hydrophilic modifier in the composition of the present invention is a functional hydrophilic polysiloxane having the general formula:

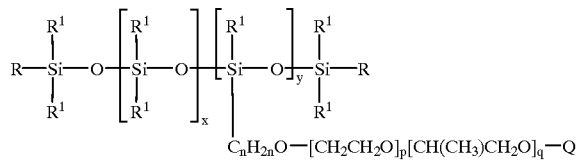

wherein functional group R is a vinyl group or a hydrogen atom, preferably a vinyl group; $R^1$ is a $C_1$ to $C_8$ univalent hydrocarbon radical, and is preferably a methyl group; Q is a hydrogen atom or a monovalent hydrocarbyl radical, preferably a methyl group; n is an integer greater than or equal to 3, preferably 3; x is an integer greater than or equal to 0, preferably from 0 to about 300; y is an integer greater than or equal to 1, preferably from about 1 to about 50; p is an integer greater than or equal to 1, preferably from about 2 to about 15; and q is an integer greater than or equal to 0, preferably from 0 to about 15.

Generally, the hydrophilic modifier can be produced by methods known in the art, for example, as disclosed in *Silicones Chemistry and Technology*, pp 111–122, CRC Press (1991), the disclosure of which is incorporated herein by reference in its entirety. An example of a preferred hydrophilic modifier for use in the composition of the present invention is commercially available from Wacker Silicones Corporation, Adrian, Mich., under the product code SLM26616, wherein R is vinyl, $R^1$ is methyl, Q is methyl, n is 3, x is about 150, y is about 20–25, p is about 3–5, and q is zero.

The amount of hydrophilic modifier introduced into the curable silicone composition should be sufficient to provide the desired benefit, for example, enhanced hydrophilicity, to the vinyl polylsiloxane impression materials. The amount of hydrophilic modifier included in the final silicone polymer material varies widely depending on the specific hydrophilic constituent involved and the degree of hydrophilicity desired. Thus, the preferred amount of hydrophilic modifier of the present invention is in the range from about 0.1% to about 30% by weight, and more preferably from about 1% to about 15% by weight, and most preferably from about 3% to about 10% by weight of the composition. The curable silicone composition contains a sufficient amount of hydrophilic modifier so that the silicone composition, when cured, has a three minute water contact angle below about 65°, and preferably has a one minute water contact angle below about 65°. The term "water contact angle" refers to the contact angle formed by a drop of distilled water and measured at a specific time after it is applied to a cured composition of the invention, as measured at room temperature using a contact angle goniometer, for example, the model 100 version made by Rame-Hart, Inc, Mountain Lakes, N.J.

The hydrophilic modifier may be used alone, or in combination with one or more surfactants in the addition-curable silicone prepolymer composition of the present invention. The surfactants used can be cationic, anionic, amphoteric or nonionic. A preferred surfactant is a nonionic type comprising nonylphenoxypoly(ethyleneoxy) ethanol, available from Rhone-Poulenc, Cranbury, N.J., under the trade names IGEPAL® CO-520, CO-530 and the like. The use of such surfactants further enhances the hydrophilicity of the cured silicone material because the nonylphenoxypoly (ethyleneoxy) ethanol is partially miscible with the hydrophilic modifier and has a synergistic effect with the modifier to improve the wettability of the cured composition.

Other additives which may be used in the present invention include plasticizers, pigments, dyes, flavors, perfumes, fluidity regulators, and the like provided that they do not substantially affect cure.

Typically, the composition according to the present invention is packaged, stored, and used in the conventional manner for addition-curable silicone prepolymer systems. Thus, the catalyst and base components are generally stored separately. The hydrophilic modifier of the present invention may be present in either component, or both. However, where the ingredients in the curable polysiloxane composition may react with constituents of either component, then it should be added only to the non-reactive component. The catalyst and base pastes are mixed together thoroughly in a ratio of from about 1:5 to about 5:1, and preferably about 1:1, and applied to the oral dentition or other region for a period of time sufficient for polymerization or hardening of the composition. Once the composition has been substantially hardened, it is removed from the mouth or other surface and used for the elaboration of casts and the like from which representations of the casting surface are subsequently prepared.

The following examples further illustrate the embodiments of the present invention. Neither these examples nor any of the foregoing disclosure should be construed as limiting in any way the scope of the present invention. Unless otherwise indicated, all parts and percentages are by weight.

EXAMPLE 1

This is a low consistency two-component composition according to the principles of the present invention, which is formulated in catalyst paste and base paste components. Mixing of each of the catalyst and base pastes is accomplished in a planetary mixer, and the resulting pastes may be milled in a three roll mill to achieve final homogeneity. The composition of each component is indicated in the table below (all quantities expressed as weight percent).

|  | Catalyst Paste | Base Paste |
|---|---|---|
| Blend of vinyl terminated polydimethylsiloxanes (200–60,000) cSt.) | 79.37 | 66.7 |
| Polymethylhydrosiloxane crosslinker (30 cSt.) | — | 8 |
| Polymerizable hydrophilic modifier (SLM 26616) | — | 5 |
| Surfactant (IGEPAL ® CO-520) | — | 1.5 |
| Platinum catalyst complex with vinylsiloxane (0.5–2.0 wt. %) | 1.5 | — |
| 1,3,5,7-tetravinyltetramethylcyclotetrasiloxane | 0.03 | — |
| Finely divided platinum metal on calcium silicate (0.5–2.0 wt. %) | 0.5 | — |
| Pigments | 0.2 | 0.4 |
| Sub-micron silica (<1 μm average particle size) | 10 | 10 |
| Calcium silicate Wollastonite (2–10 μm average particle size) | 8.4 | 8.4 |
| Total | 100 | 100 |

EXAMPLE 2

This is a medium consistency two-component composition according to the principles of the present invention having moderate thixotropy, which is formulated in catalyst paste and base paste components. Mixing of each of the catalyst and base pastes is accomplished in a planetary mixer, and the resulting pastes may be milled in a three roll mill to achieve final homogeneity. The composition of each component is indicated in the table below.

|  | Catalyst Paste | Base Paste |
|---|---|---|
| Blend of vinyl terminated polydimethylsiloxanes (200–60,000) cSt.) | 70.27 | 60.5 |
| Polymethylhydrosiloxane crosslinker (30 cSt.) | — | 8 |
| Polymerizable hydrophilic modifier (SLM 26616) | — | 5 |
| Surfactant (IGEPAL ® CO-520) | — | 1.5 |
| Platinum catalyst complex with vinylsiloxane (0.5–2.0 wt. %) | 1.5 | — |
| 1,3,5,7-tetravinyltetramethylcyclotetrasiloxane | 0.03 | — |
| Finely divided platinum metal on calcium silicate (0.5–2.0 wt. %) | 0.5 | — |
| Pigments | 0.25 | 0.5 |
| Sub-micron silica (<1 μm average particle size) | 16 | 16 |
| Calcium silicate Wollastonite (2–10 μm average particle size) | 11.45 | 8.5 |
| Total | 100 | 100 |

EXAMPLE 3

This is a high consistency two-component composition according to the principles of the present invention having high thixotropy, which is formulated in catalyst paste and base paste components. Mixing of each of the catalyst and base pastes is accomplished in a planetary mixer, and the resulting pastes may be milled in a three roll mill to achieve final homogeneity. The composition of each component is indicated in the table below.

|  | Catalyst Paste | Base Paste |
|---|---|---|
| Blend of vinyl terminated polydimethylsiloxanes (200–60,000) cSt.) | 64.27 | 58 |
| Polymethylhydrosiloxane crosslinker (30 cSt.) | — | 8 |
| Polymerizable hydrophilic modifier (SLM 26616) | — | 5 |
| Surfactant (IGEPAL ® CO-520) | — | 1.5 |
| Platinum catalyst complex with vinylsiloxane (0.5–2.0 wt. %) | 1.5 | — |
| 1,3,5,7-tetravinyltetramethylcyclotetrasiloxane | 0.03 | — |
| Finely divided platinum metal on calcium silicate (0.5–2.0 wt. %) | 0.5 | — |
| Pigments | 0.38 | 0.5 |
| Sub-micron silica (<1 μm average particle size) | 20 | 19 |
| Calcium silicate Wollastonite (2–10 μm average particle size) | 13.32 | 8 |
| Total | 100 | 100 |

EXAMPLE 4

In comparison with Example 1, this example illustrates the effect of the addition of a non-polymerizable hydrophilic additive, such as an ethoxylated surfactant SILWET® L-77, available from Witco Corp., Greenwich, Conn., and generally described in U.S. Pat. No. 4,657,959 into the silicone composition. As will be shown in the table below, use of this additive results in poor physical properties in the cured composition even though a high wetting capability and low water contact angle are achieved. The catalyst and base pastes are prepared as described in Example 1. The composition of each component is indicated in the table below.

|  | Catalyst Paste | Base Paste |
|---|---|---|
| Blend of vinyl terminated polydimethylsiloxanes (200–60,000) cSt.) | 79.47 | 68.75 |

-continued

| | Catalyst Paste | Base Paste |
|---|---|---|
| Polymethylhydrosiloxane crosslinker (30 cSt.) | — | 8 |
| Hydrophilic additive (SILWET ® L-77) | — | 5 |
| Surfactant (IGEPAL ® CO-520) | — | 0 |
| Platinum catalyst complex with vinylsiloxane (0.5–2.0 wt. %) | 1.5 | — |
| 1,3,5,7-tetravinyltetramethylcyclotetrasiloxane | 0.03 | — |
| Finely divided platinum metal on calcium silicate (0.5–2.0 wt. %) | 0.5 | — |
| Pigments | 0.5 | 0.25 |
| Sub-micron silica (<1 μm average particle size) | 10 | 10 |
| Calcium silicate Wollastonite (2–10 μm average particle size) | 8 | 8 |
| Total | 100 | 100 |

EXAMPLE 5

In comparison with Example 1, this example again illustrates the effect of the addition of a non-polymerizable hydrophilic additive into the silicone composition. As will be shown in the table below, use of this additive results in poor physical properties in the cured composition even though a high wetting capability and low water contact angle are achieved. The catalyst and base pastes are prepared as described in Example 1. The composition of each component is indicated in the table below.

| | Catalyst Paste | Base Paste |
|---|---|---|
| Blend of vinyl terminated polydimethylsiloxanes (200–60,000) cSt.) | 79.47 | 66.25 |
| Polymethylhydrosiloxane crosslinker (30 cSt.) | — | 8 |
| Hydrophilic additive (SILWET ® L-77) | — | 5 |
| Surfactant (IGEPAL ® CO-520) | — | 0 |
| Platinum catalyst complex with vinylsiloxane (0.5–2.0 wt. %) | 1.5 | — |
| 1,3,5,7-tetravinyltetramethylcyclotetrasiloxane | 0.03 | — |
| Finely divided platinum metal on calcium silicate (0.5–2.0 wt. %) | 0.5 | — |
| Pigments | 0.5 | 0.25 |
| Sub-micron silica (<1 μm average particle size) | 10 | 10 |
| Calcium silicate Wollastonite (2–10 μm average particle size) | 8 | 8 |
| Total | 100 | 100 |

EXAMPLES 1–5

A representative sample of each paste composition for each of the above-described examples is mixed accordingly in equal volumes. The physical properties of the cured compositions are determined, using ISO Specification No. 4823 for evaluation of work time, set time, mixed consistency, dimensional change, strain in compression and deformation recovery; and ASTM Standards for the evaluation of shore A hardness (ASTM D2240), tensile strength (ASTM D412), elongation (ASTM D412) and tear strength (ASTM 624). The water contact angle is measured at 60 seconds after a drop of distilled water is applied to a cured composition of the invention, at room temperature using a contact angle goniometer (model 100 made by Rame-Hart, Inc.). The results are reported in the following table.

| | Example | | | | |
|---|---|---|---|---|---|
| | 1 | 2 | 3 | 4 | 5 |
| Work time (min.) | 1.5 | 1.5 | 1.5 | 1.5 | 1.7 |
| Set time (min.) | 4 | 4 | 4 | 4 | 4 |
| Mixed consistency (mm) | 43 | 31.3 | 27 | — | — |
| Dimensional change at 24 hr. (%) | 0.16 | 0.33 | 0.28 | 0.33 | 0.3 |
| Strain in compression (%) | 4.7 | 4.5 | 4.35 | 5.8 | — |
| Deformation recovery (%) | 99.8 | 99.7 | 99.7 | 99.6 | 98.57 |
| Hardness (Shore A) | 40 | 50 | 67 | 36 | 36 |
| Tensile strength (Mpa) | 2.52 | 3.5 | 3.81 | 1.84 | 1.68 |
| Elongation (%) | 400 | 406 | 420 | 392 | 428 |
| Tear Strength (Die C) (N/mm) | 5.27 | 7.7 | 9.37 | 5.22 | 4.69 |
| Contact angle (at 1 min.) (deg.) | 26 | 29 | 31 | 8 | 7 |

While the present invention has been illustrated by the description of an embodiment thereof, and while the embodiment has been described in considerable detail, it is not intended to restrict or in any way limit the scope of the appended claims to such detail. Additional advantages and modifications will readily appear to those skilled in the art. The invention in its broader aspects is therefore not limited to the specific details, representative method and illustrative examples shown and described. Accordingly, departures may be made from such details without departing from the scope or spirit of applicant's general inventive concept.

What is claimed is:

1. A curable silicone composition for use as a dental impression material, comprising:
   an addition-curable silicone prepolymer comprising an organopolysiloxane polymer; and
   at least one polymerizable hydrophilic modifier that is miscible with the organopolysiloxane polymer and that is a functional hydrophilic polysiloxane having a general formula of:

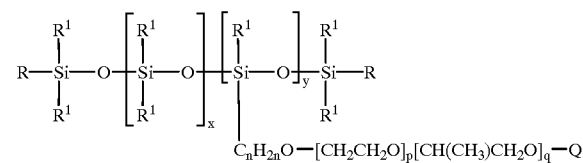

wherein functional group R is a vinyl group or a hydrogen atom; $R^1$ is a $C_1$ to $C_8$ univalent hydrocarbon radical; Q is a hydrogen atom or a monovalent hydrocarbyl radical; n is an integer greater than or equal to three; x is an integer greater than or equal to zero; y is an integer greater than or equal to one; p is an integer greater than or equal to one; and q is an integer greater than or equal to zero.

2. The composition of claim 1, wherein the addition-curable silicone prepolymer comprises: (a) at least one vinyl terminated organopolysiloxane fluid; (b) at least one organohydrogen polysiloxane crosslinker; (c) a noble metal-based catalyst; (d) a retarder; and (e) filler.

3. The composition of claim 2, wherein the composition is a paste/paste system including a catalyst paste and a base paste, the catalyst paste comprising (a) at least one vinyl terminated organopolysiloxane fluid, (b) the noble metal-based catalyst, (c) the retarder, (d) a hydrogen scavenger and (e) filler; and the base paste comprising (a) at least one vinyl terminated organopolysiloxane fluid, (b) at least one organohydrogen polysiloxane crosslinker, (c) the hydrophilic modifier, and (d) filler.

4. The composition of claim 2, wherein the vinyl terminated organopolysiloxane fluid comprises at least two vinyl groups per molecule bonded directly to silicon atoms.

5. The composition of claim 4, wherein the vinyl terminated organopolysiloxane fluid comprises linear vinyl terminated organopolysiloxane having organo substituents selected from the group consisting of: alkyl, aryl, halogen, and combinations thereof.

6. The composition of claim 5, wherein the vinyl terminated organopolysiloxane fluid comprises at least one vinyl terminated polydimethylsiloxane fluid.

7. The composition of claim 6, wherein the at least one vinyl terminated polydimethylsiloxane fluid includes a blend of fluids having different molecular weights, each fluid having a viscosity in the range of about 100 to about 100,000 centistoke.

8. The composition of claim 2, wherein the organohydrogen polysiloxane crosslinker comprises organopolysiloxane having at least three hydrogen atoms per molecule bonded directly to silicon atoms, and having organo substituents selected from the group consisting of: alkyl, aryl, halogen, and combinations thereof.

9. The composition of claim 8, wherein the crosslinker is an organohydrogen polysiloxane selected from the group consisting of polymethylhydrosiloxane, methylhydro dimethyl polysiloxane copolymer, and combinations thereof.

10. The composition of claim 9, wherein the polymethylhydrosiloxane has a viscosity range of about 2 to about 300 centistoke.

11. The composition of claim 2, wherein the noble metal-based catalyst is a platinum-based catalyst.

12. The composition of claim 2, wherein the retarder is a polysiloxane fluid selected from the group consisting of: low molecular weight, vinyl functional linear polysiloxane and low molecular weight, vinyl functional cyclic polysiloxane.

13. The composition of claim 2, wherein the filler is present in an amount of about 15 to about 50 wt. % of the composition.

14. The composition of claim 13, wherein the filler is a blend of sub-micron sized filler particles and micron sized filler particles.

15. The composition of claim 2, further comprising a hydrogen scavenger.

16. The composition of claim 1, wherein R is a vinyl group, and $R^1$ and Q are methyl groups.

17. The composition of claim 1, wherein n equals 3, x equals 0 to about 300, y equals about 1 to about 50, p equals about 2 to about 15, and q equals 0 to about 15.

18. The composition of claim 1, wherein R is a vinyl group, $R^1$ and Q are methyl groups, n equals 3, x equals about 150, y equals about 20 to 25, p equals about 3 to about 5, and q equals 0.

19. The composition of claim 1, wherein the hydrophilic modifier is present in an amount of about 0.1 to about 30 wt. % of the composition.

20. The composition of claim 1, wherein the hydrophilic modifier is present in an amount sufficient to achieve a three minute water contact angle below about 65° in the composition after curing.

21. A curable silicone composition for use as a dental impression material, comprising:
an addition-curable silicone prepolymer;
at least one polymerizable hydrophilic modifier that is a functional hydrophilic polysiloxane having a general formula of:

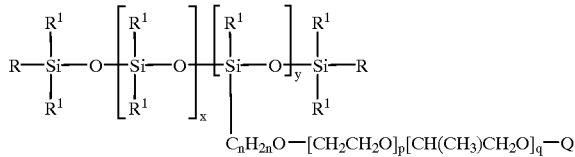

wherein functional group R is a vinyl group or a hydrogen atom; $R^1$ is a $C_1$ to $C_8$ univalent hydrocarbon radical; Q is a hydrogen atom or a monovalent hydrocarbyl radical; n is an integer greater than or equal to three; x is an integer greater than or equal to zero; y is an integer greater than or equal to one; p is an integer greater than or equal to one; and q is an integer greater than or equal to zero; and
a surfactant, wherein the surfactant is at least partially miscible with the hydrophilic modifier.

22. The composition of claim 21, wherein the surfactant is nonylphenoxypoly (ethyleneoxy) ethanol.

23. A method of making a dental impression comprising the step of making a negative mold of oral tissue using a curable silicone composition of claim 1.

24. A method of making a dental impression comprising the step of making a negative mold of oral tissue using a curable silicone composition of claim 2.

25. A method of making a dental impression comprising the step of making a negative mold of oral tissue using a curable silicone composition of claim 3.

26. A method of making a dental impression comprising the step of making a negative mold of oral tissue using a curable silicone composition of claim 21.

27. A dental impression comprising a cured silicone composition of claim 1.

28. A dental impression comprising a cured silicone composition of claim 2.

29. A dental impression comprising a cured silicone composition of claim 3.

30. A dental impression comprising a cured silicone composition of claim 21.

31. The composition of claim 1, further comprising a surfactant, wherein the surfactant is at least partially miscible with the hydrophilic modifier.

32. A curable silicone composition for use as a dental impression material, comprising:
an addition-curable silicone prepolymer including a filler, the filler comprising about 15 to about 50% of the composition and comprising a blend of sub-micron sized filler particles and micron sized filler particles;
at least one polymerizable hydrophilic modifier that is a functional hydrophilic polysiloxane having a general formula of:

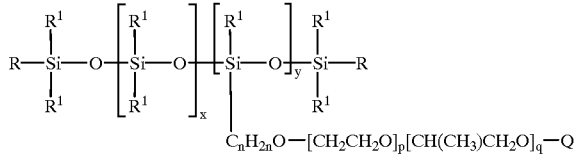

wherein functional group R is a vinyl group or a hydrogen atom; $R^1$ is a $C_1$ to $C_8$ univalent hydrocarbon radical; Q is a hydrogen atom or a monovalent hydrocarbyl radical; n is an integer greater than or equal to three; x is an integer greater than or equal to zero; y is an integer greater than or equal to one; p is an integer greater than or equal to one; and q is an integer greater than or equal to zero.

33. A curable silicone composition for use as a dental impression material, comprising:
 a paste/paste system including a catalyst paste and a base paste, the catalyst paste comprising (a) at least one vinyl terminated organopolysiloxane fluid, (b) a noble metal-based catalyst, (c) a retarder, (d) a hydrogen scavenger and (e) filler; and the base paste comprising (a) at least one vinyl terminated organopolysiloxane fluid, (b) at least one organohydrogen polysiloxane crosslinker, (c) a polymerizable hydrophilic modifier, and (d) filler,
 wherein the polymerizable hydrophilic modifier is a functional hydrophilic polysiloxane having a general formula of:

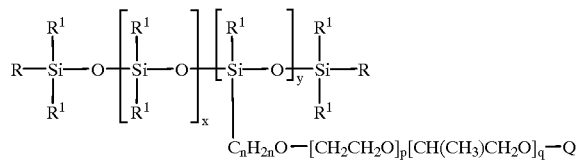

wherein functional group R is a vinyl group or a hydrogen atom; $R^1$ is a $C_1$ to $C_8$ univalent hydrocarbon radical; Q is a hydrogen atom or a monovalent hydrocarbyl radical; n is an integer greater than or equal to three; x is an integer greater than or equal to zero; y is an integer greater than or equal to one; p is an integer greater than or equal to one; and q is an integer greater than or equal to zero.

* * * * *

UNITED STATES PATENT AND TRADEMARK OFFICE
CERTIFICATE OF CORRECTION

PATENT NO. : 6,201,038 B1  
DATED : March 13, 2001  
INVENTOR(S) : Duncan E. Waller and Xiaoyi Xie It is certified that error appears in the above-identified patent and that said Letters Patent is hereby corrected as shown below:

<u>Title page,</u>  
Item [56], References Cited, U.S. PATENT DOCUMENTS, add the following:

| | | | |
|---|---|---|---|
| -- 4,035,453 | 07/1977 | Hittmair et al. | 264/16 |
| 4,340,647 | 07/1982 | Eckberg | 428/429 |
| 4,657,959 | 04/1987 | Bryan et al. | 524/266 |
| 4,691,039 | 09/1987 | Aasen et al. | 556/446 |
| 4,752,633 | 06/1988 | Aasen et al. | 524/266 |
| 5,064,891 | 11/1991 | Fujiki et al. | 524/264 |
| 5,086,148 | 02/1992 | Jochum et al. | 528/15 |
| 5,367,001 | 11/1994 | Itoh et al. | 523/109 |
| 5,583,178 | 12/1996 | Oxman et al. | 524/862 |
| 5,596,025 | 01/1997 | Oxman et al. | 523/109 |
| 5,637,628 | 06/1997 | Kamohara et al. | 523/109 |
| 5,661,222 | 08/1997 | Hare | 525/478 |
| 5,684,060 | 11/1997 | Konings et al. | 523/109 |
| 5,750,589 | 05/1998 | Zech et al. | 523/109 |
| 5,830,951 | 11/1998 | Fiedler | 525/478 |
| 5,862,068 | 12/1998 | Jada | 523/109 |
| 5,863,965 | 01/1999 | Hare | 523/109 |
| 5,863,969 | 01/1999 | Ward et al. | 523/213 -- |

FOREIGN PATENT DOCUMENTS, add the following:

| | | |
|---|---|---|
| -- 0231420B1 | 9/1991 | European Patent Off. |
| 4129613 | 3/1993 | Gemany |
| 93/17654 | 9/1993 | WIPO |
| 4433139 | 3/1996 | Germany |
| 19525468 | 1/1997 | Germany |
| 98/53791 | 12/1998 | WIPO |
| 0885932A2 | 12/1998 | European Patent Off. -- |

UNITED STATES PATENT AND TRADEMARK OFFICE
CERTIFICATE OF CORRECTION

PATENT NO. : 6,201,038 B1
DATED : March 13, 2001
INVENTOR(S) : Duncan E. Waller and Xiaoyi Xie It is certified that error appears in the above-identified patent and that said Letters Patent is hereby corrected as shown below:

Title page (cont'd),
OTHER PUBLICATIONS, add the following:
-- "Silicones, Chemistry and Technology", CRC Press (1991), pp. 111-122. --

Signed and Sealed this

Twenty-sixth Day of October, 2004

JON W. DUDAS
*Director of the United States Patent and Trademark Office*

UNITED STATES PATENT AND TRADEMARK OFFICE
CERTIFICATE OF CORRECTION

PATENT NO. : 6,201,038 B1
DATED : March 13, 2001
INVENTOR(S) : Duncan E. Waller and Xiaoyi Xie It is certified that error appears in the above-identified patent and that said Letters Patent is hereby corrected as shown below:

<u>Title page,</u>
Item [56], References Cited, U.S. PATENT DOCUMENTS, add the following:

| | | | |
|---|---|---|---|
| -- 4,035,453 | 07/1977 | Hittmair et al. | 264/16 |
| 4,340,647 | 07/1982 | Eckberg | 428/429 |
| 4,657,959 | 04/1987 | Bryan et al. | 524/266 |
| 4,691,039 | 09/1987 | Aasen et al. | 556/446 |
| 4,752,633 | 06/1988 | Aasen et al. | 524/266 |
| 5,064,891 | 11/1991 | Fujiki et al. | 524/264 |
| 5,086,148 | 02/1992 | Jochum et al. | 528/15 |
| 5,367,001 | 11/1994 | Itoh et al. | 523/109 |
| 5,583,178 | 12/1996 | Oxman et al. | 524/862 |
| 5,596,025 | 01/1997 | Oxman et al. | 523/109 |
| 5,637,628 | 06/1997 | Kamohara et al. | 523/109 |
| 5,661,222 | 08/1997 | Hare | 525/478 |
| 5,684,060 | 11/1997 | Konings et al. | 523/109 |
| 5,750,589 | 05/1998 | Zech et al. | 523/109 |
| 5,830,951 | 11/1998 | Fiedler | 525/478 |
| 5,852,068 | 12/1998 | Jada | 523/109 |
| 5,863,965 | 01/1999 | Hare | 523/109 |
| 5,863,969 | 01/1999 | Ward et al. | 523/213 -- |

FOREIGN PATENT DOCUMENTS, add the following:

| | | |
|---|---|---|
| -- 0231420B1 | 9/1991 | European Patent Off. |
| 4129613 | 3/1993 | Gemany |
| 93/17654 | 9/1993 | WIPO |
| 4433139 | 3/1996 | Germany |
| 19525468 | 1/1997 | Germany |
| 98/53791 | 12/1998 | WIPO |
| 0885932A2 | 12/1998 | European Patent Off. -- |

UNITED STATES PATENT AND TRADEMARK OFFICE
CERTIFICATE OF CORRECTION

PATENT NO. : 6,201,038 B1
DATED : March 13, 2001
INVENTOR(S) : Duncan E. Waller and Xiaoyi Xie It is certified that error appears in the above-identified patent and that said Letters Patent is hereby corrected as shown below:

<u>Title page (cont'd),</u>
OTHER PUBLICATIONS, add the following:
-- "Silicones, Chemistry and Technology", CRC Press (1991), pp. 111-122. --

This certificate supersedes Certificate of Correction issued October 26, 2004.

Signed and Sealed this

Third Day of May, 2005

JON W. DUDAS
*Director of the United States Patent and Trademark Office*